(12) United States Patent
Neiss et al.

(10) Patent No.: US 7,471,386 B2
(45) Date of Patent: Dec. 30, 2008

(54) SYSTEM AND METHOD FOR SPECTRAL UNMIXING IN A FIBER ARRAY SPECTRAL TRANSLATOR BASED POLYMORPH SCREENING SYSTEM

(75) Inventors: Jason H. Neiss, Pittsburgh, PA (US); Patrick J. Treado, Pittsburgh, PA (US); Robert Schweitzer, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 139 days.

(21) Appl. No.: 11/679,112

(22) Filed: Feb. 26, 2007

(65) Prior Publication Data

US 2007/0201022 A1    Aug. 30, 2007

Related U.S. Application Data

(60) Provisional application No. 60/777,219, filed on Feb. 27, 2006.

(51) Int. Cl.
*G01J 3/00* (2006.01)

(52) U.S. Cl. .................. 356/300; 356/301; 356/328

(58) Field of Classification Search .................. 356/300, 356/301, 328
See application file for complete search history.

(56) References Cited

U.S. PATENT DOCUMENTS

| | | | |
|---|---|---|---|
| 4,781,458 A | 11/1988 | Angel et al. | |
| 5,534,997 A | 7/1996 | Schrader | |
| 5,615,673 A | 4/1997 | Berger et al. | |
| 5,963,319 A | 10/1999 | Jarvis et al. | |
| 6,100,975 A | 8/2000 | Smith et al. | |
| 6,483,581 B1 | 11/2002 | Ben-Amotz et al. | |
| 6,486,948 B1 | 11/2002 | Zeng | |
| 6,867,858 B2 | 3/2005 | Owen et al. | |
| 7,072,770 B1 | 7/2006 | Schweitzer et al. | |
| 2002/0048610 A1 | 4/2002 | Cima et al. | |
| 2003/0059837 A1 | 3/2003 | Levinson et al. | |
| 2003/0162226 A1 | 8/2003 | Cima et al. | |
| 2005/0089923 A9 | 4/2005 | Levinson et al. | |
| 2005/0095696 A9 | 5/2005 | Lemmo et al. | |
| 2005/0191614 A1 | 9/2005 | Cima et al. | |
| 2006/0124443 A1* | 6/2006 | Tuschel et al. | 204/157.92 |
| 2008/0151225 A1* | 6/2008 | Treado et al. | 356/73 |

OTHER PUBLICATIONS

Manolakis, D. et al., "Hyperspectral Subpixel Target Detection Using the Linear Mixing Model," IEEE Trans. on Geoscience and Remote Sensing, Jul. 2001, V. 39, No. 7, p. 1392-1409.

Anquetil, P., et al. "Laser Raman Spectroscopic Analysis of Polymorphic Forms in Microliter Fluid Volumes," J. of Pharma. Sciences, Jan. 2003, V. 92, No. 1, pp. 149-161.

(Continued)

*Primary Examiner*—F. L Evans
(74) *Attorney, Agent, or Firm*—Duane Morris LLP

(57) ABSTRACT

The disclosure relates generally to methods and apparatus for using a fiber array spectral translator-based ("FAST") spectroscopic system for performing spectral unmixing of a mixture containing multiple polymorphs. In an embodiment, a first spectrum of a mixture containing polymorphs of a compound is obtained using a photon detector and a fiber array spectral translator having plural fibers. A set of second spectra is provided where each spectrum of the set of second spectra may be representative of a different polymorph of the compound. The first spectrum and the set of second spectra may be compared, and based on the comparison, the presence of one or more polymorphs in the mixture may be determined.

44 Claims, 10 Drawing Sheets

OTHER PUBLICATIONS

Carter, J.C., et al., Multi-Wavelength Raman Imaging Using a Small-Diameter Image Guide with a Dimension-Reduction Imaging Array, Appl. Spectro, 2003, V57, No. 7, pp. 761-767.

Ma, Jiaying and Ben-Amotz, Dor, "Rapid Micro-Raman Imaging Using Fiber-Bundle Image Compression," Applied Spectroscopy; 1997, V. 51, No. 12, pp. 1845-1849.

Nelson, M. et al., Single-Frame Chemical Imaging: Dimens. Reduction Fiber-Optic Array Improvements & Appl. to Laser-Induced Breakdown Spectroscopy, 1999, V53, #7, pp. 751-759.

Nelson, M. et al. "Single-Shot Multiwavelength Imageing of Laser Plumes," Applied Spectroscopy, 1998, V. 52, No. 2, pp. 179-187.

* cited by examiner

SYSTEM AND METHOD FOR SPECTRAL UNMIXING IN A FIBER ARRAY SPECTRAL TRANSLATOR BASED POLYMORPH SCREENING SYSTEM

PRIORITY INFORMATION

The instant disclosure claims the filing-date benefit of Provisional Application No. 60/777,219 filed 27 Feb. 2006, entitled "Spectral Unmixing in a Fiber Array Spectral Translator (FAST) Based Polymorph Screening", the disclosure of which is incorporated herein in its entirety.

BACKGROUND

A fiber array spectral translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector.

Given the advantageous ability of a FAST system to acquire hundreds to thousands of full spectral range, spatially-resolved spectra, such as Raman spectra, substantially simultaneously, a FAST system may be used in a variety of situations to help resolve difficult spectrographic problems such as the presence of polymorphs of a compound, sometimes referred to as spectral unmixing. As is known in the art, polymorphs may typically have a unique spectrum, such as a Raman spectrum, and the ability to rapidly determine the existence, or non-existence, of one or more polymorphs is essential to ensure, for example, the safety of a given compound when certain polymorphs may be hazardous to personnel and/or equipment.

Accordingly, it is an object of the present disclosure to provide a method for spectral unmixing, comprising obtaining a first spectrum of a mixture containing polymorphs of a compound using a photon detector and a fiber array spectral translator having plural fibers, providing a set of second spectra wherein each spectrum of said set of second spectra is representative of a different polymorph of said compound, comparing said first spectrum with said set of second spectra, and determining the presence of one or more polymorphs in said mixture based on said comparison.

It is another object of the present disclosure to provide a system for spectral umixing, comprising a photon source for illuminating with first photons a mixture containing polymorphs of a compound to thereby produce second photons, a fiber array spectral translator having plural fibers, wherein said fiber array spectral translator receives said second photons, a photon detector operatively connected to said fiber array spectral translator, wherein said photon detector detects said second photons to thereby obtain a first spectrum, and a microprocessor unit operatively connected to said photon detector and to a memory unit, wherein said memory unit stores a set of second spectra wherein each spectrum of said set of second spectra is representative of a different polymorph of said compound, and wherein said microprocessor compares said first spectrum with said set of second spectra to thereby determine the presence of one or more polymorphs in said mixture based on said comparison.

It is a further object of the present disclosure to provide a method for spectral umixing, comprising obtaining a first spectrum of a mixture containing polymorphs of a compound using a photon detector and a fiber array spectral translator having plural fibers, wherein said first spectrum is obtained from one of said plural fibers, providing a set of second spectra wherein each spectrum of said set of second spectra is representative of a different polymorph of said compound, comparing said first spectrum with said set of second spectra using a linear spectral unmixing algorithm, determining a set of mixture coefficients to thereby determine the presence of one or more polymorphs in said mixture, determining a goodness-of-fit factor and comparing said goodness-of-fit factor to a predetermined threshold, and determining the presence of an unknown substance in said mixture if said goodness-of-fit factor is less than said predetermined threshold.

It is yet a further object of the present disclosure to provide a system for spectral unmixing, comprising a photon source for illuminating with first photons a mixture containing polymorphs of a compound to thereby produce second photons, a fiber array spectral translator having plural fibers, wherein one fiber of said fiber array spectral translator receives said second photons, a photon detector operatively connected to said one fiber of said fiber array spectral translator, wherein said photon detector detects said second photons to thereby obtain a first spectrum, and a microprocessor unit operatively connected to said photon detector and to a memory unit, wherein said memory unit stores a set of second spectra wherein each spectrum of said set of second spectra is representative of a different polymorph of said compound, and wherein said microprocessor includes circuitry for comparing said first spectrum with said set of second spectra using a linear spectral unmixing algorithm to thereby determine a set of mixture coefficients so as to determine the presence of one or more polymorphs in said mixture based on said comparison, circuitry for determining a goodness-of-fit factor and comparing said goodness-of-fit factor to a predetermined threshold, and circuitry for determining the presence of an unknown substance in said mixture if said goodness-of-fit factor is less than said predetermined threshold.

It is still a further object of the present disclosure to provide a system for spectral unmixing, comprising a photon source for illuminating with first photons a mixture containing polymorphs of a compound to thereby produce second photons, a fiber array spectral translator having plural fibers, wherein one fiber of said fiber array spectral translator receives said second photons, a photon detector operatively connected to said one fiber of said fiber array spectral translator, wherein said photon detector detects said second photons to thereby obtain a first spectrum, and a microprocessor unit operatively connected to said photon detector and to a memory unit, wherein said memory unit stores a set of second spectra wherein each spectrum of said set of second spectra is representative of a different polymorph of said compound, and wherein said microprocessor runs a software program for comparing said first spectrum with said set of second spectra using a linear spectral unmixing algorithm to thereby determine a set of mixture coefficients so as to determine the presence of one or more polymorphs in said mixture based on said comparison, determining a goodness-of-fit factor and comparing said goodness-of-fit factor to a predetermined threshold, and determining the presence of an unknown substance in said mixture if said goodness-of-fit factor is less than said predetermined threshold.

DETAILED DESCRIPTION

Figure 1:
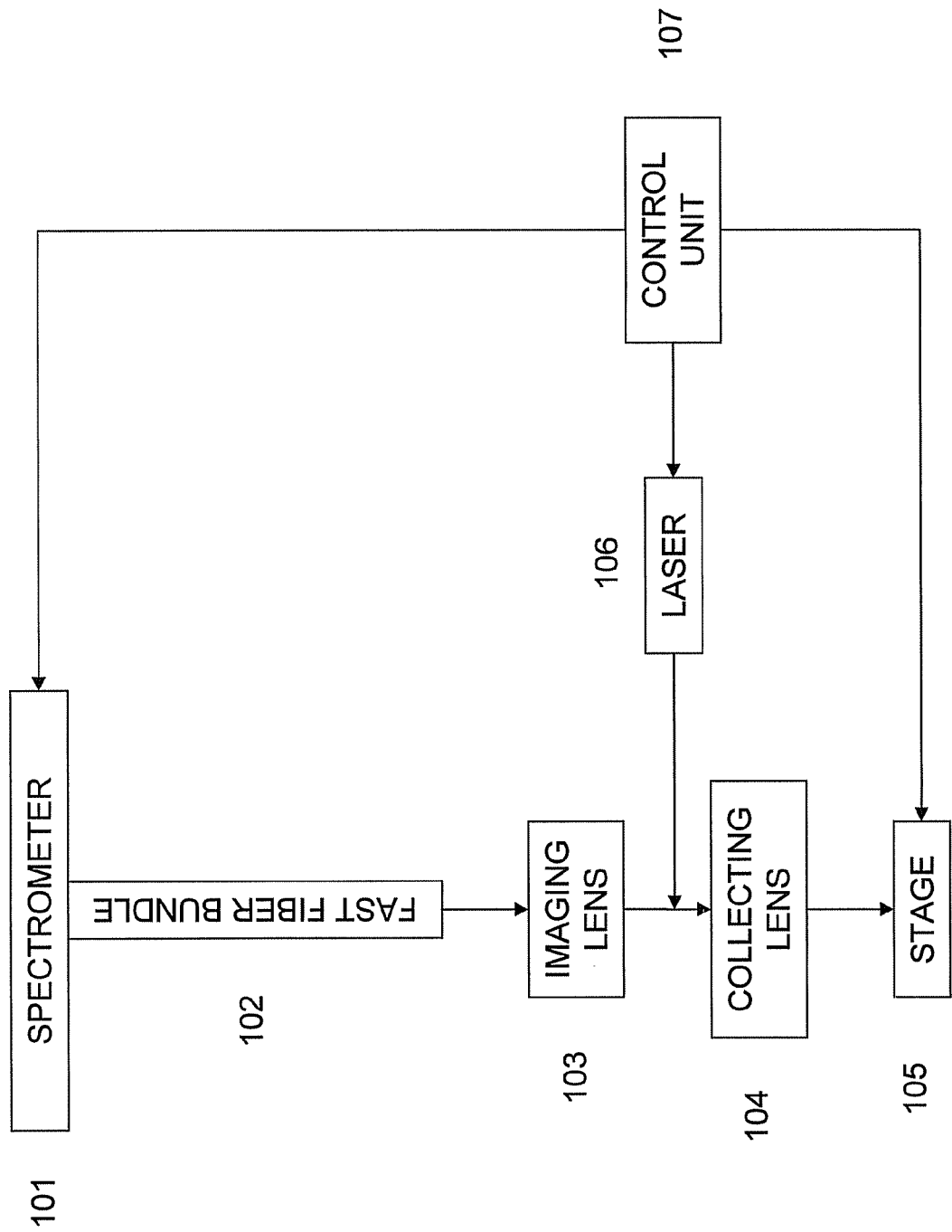
FIG. 1 is a schematic block diagram of a of a fiber array spectral translator ("FAST") based spectroscopy system.
Figure 2:
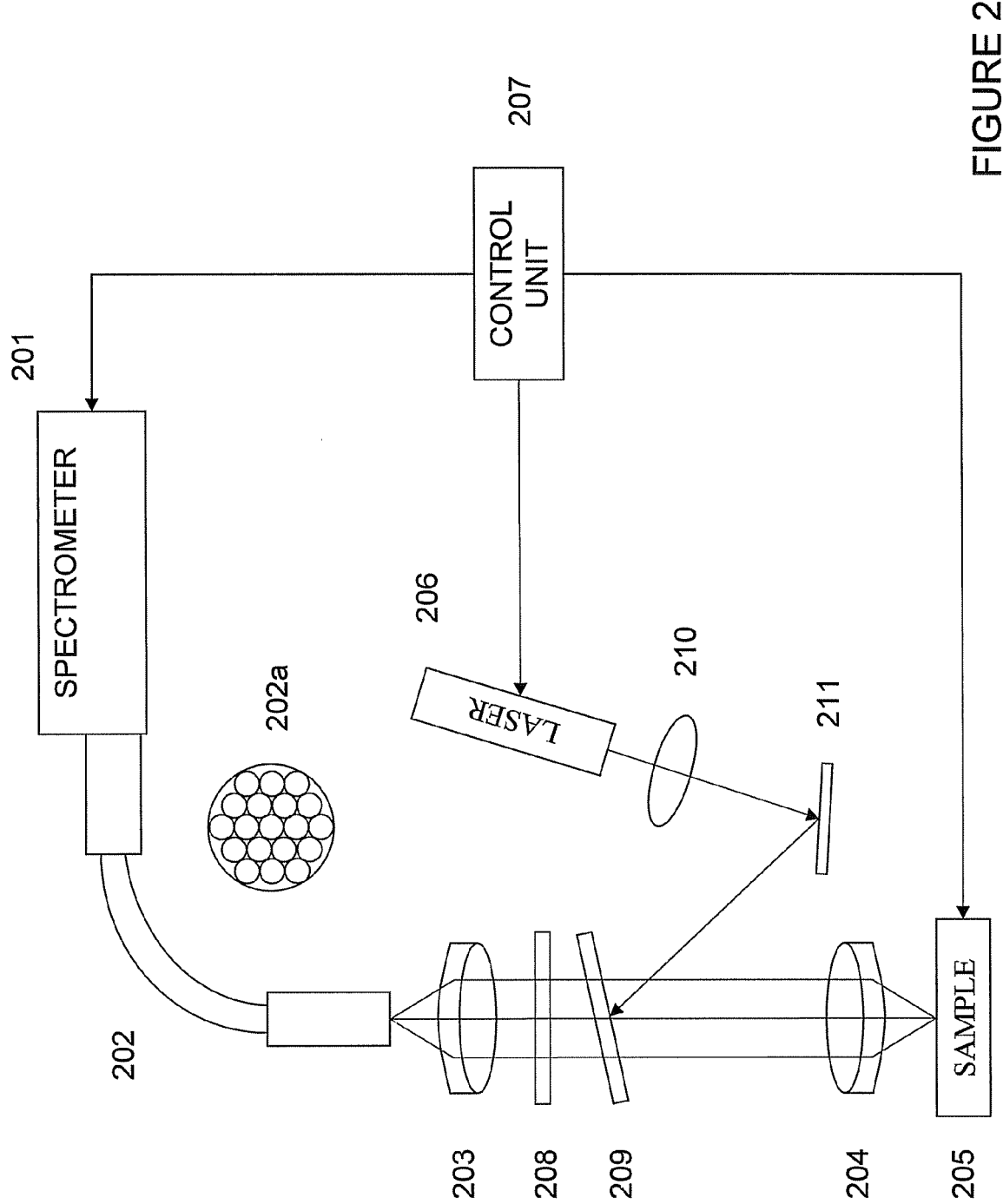
FIG. 2 is a is a schematic drawing of a FAST based spectroscopy system.
Figure 3:
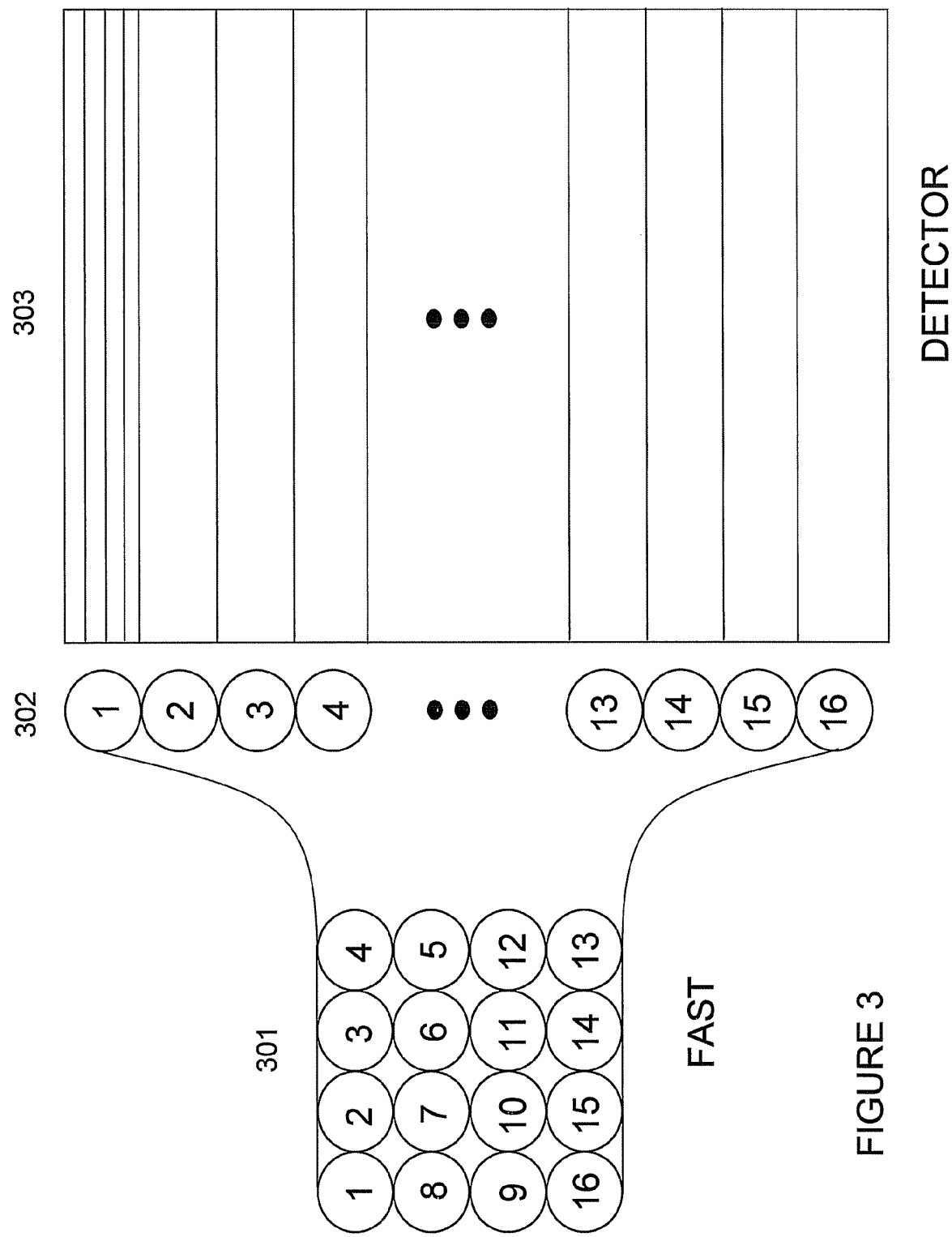
FIG. 3 is a schematic drawing of a fiber array spectral translator showing an exemplary spatial mapping arrangement.

FIG. 1 illustrates a block diagram of an exemplary FAST-based spectroscopy system including a spectrometer 101, a FAST fiber bundle 102, an imaging lens 103, a collecting lens 104, a stage 105 for holding, e.g., a 96-well plate containing samples which may be a mixture containing polymorphs of a compound, a photon source 106, such as the laser shown, and a control unit 107 for controlling the spectrometer 101, the photon source 106 and the stage 105. FIG. 2, on the other hand, provides a more detailed architectural view of the FAST system illustrated in FIG. 1. In FIG. 2, the system may include a spectrometer 201, a FAST fiber bundle 202, which may be arranged in a substantially circular, 19 fiber arrangement as shown in 202a, an lens 203, which may be an imaging lens, a lens 204, which may be a collecting lens, sample 205 which may be mounted in a well of a well plate, such as the stage 105 described above with respect to FIG. 1, a photon source 206, which may be a laser as shown, a control unit 207, which may control the spectrometer 201, the laser 206, and the sample 205, a filter 208 which may be a 0° filter such as a laser rejection filter, a filter 209 which may be a 7° filter, such as a laser rejection filter, a lens 210, which may be a focusing lens, and a mirror 211. A FAST system may also be referred to as Dimension Reduction Arrays. FAST technology can acquire hundreds to thousands of full spectral range, spatially resolved Raman spectra simultaneously. This is accomplished by focusing an image onto a two dimensional array of optical fibers (at that end of the fiber bundle which is proximal to the sample to be viewed) such as the FAST fiber bundle 202 that are drawn into a one dimensional distal array (at that end of the fiber bundle which feeds the optical signals into the spectrometer/spectrograph, i.e., where the FAST fiber bundle 202 enters the spectrometer 201) with serpentine (or curvilinear) ordering as illustrated in FIG. 3. The one dimensional fiber stack is coupled to an imaging spectrograph 201. Software and/or hardware may then extract the spectral/spatial information that is embedded in a single CCD image frame.

Referring now to FIG. 3, the construction of the FAST array requires knowledge of the position of each fiber at both the imaging end and the distal end of the array as shown, for example, in the simplified diagram for FIG. 3 where a total of sixteen fibers are shown numbered in correspondence between the imaging (or proximal) end 301 and the distal end 302 of the fiber bundle. As shown in FIG. 3, a FAST fiber bundle may feed optical information from its 2D non-linear imaging end 301 (which can be in any non-linear configuration, e.g., circular, square, rectangular, etc.) to its 2D linear distal end 302, which feeds the optical information into associated detector rows 303. The distal end may be positioned at the input to a photon detector 303, such as a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

FIG. 3 shows a non-limiting exemplary spatial arrangement of fibers at the imaging end 301 and the distal end 302. Additionally, as shown in FIG. 3, each fiber may span more than one detector row in detector 303, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

Thus, in the FAST application, a fiber bundle is physically organized in 2-D (X-Y) at the signal input end so as to image the sample in 2D. On the output side, however, the fibers in the fiber bundle are stacked in a linear or curvilinear array (1D) (principally X or Y direction only depending on the slit placement) and aligned with a slit in the grating-based spectrometer so as to facilitate extraction of spectral info. It is known that a spectrometer works on a liner (1D) input. This 1D output from the fiber bundle is fed to the spectrometer gratings (or other similar dispersive elements) to separate signal wavelengths. Each wavelength-dispersed signal (1D) from the gratings may be sent to the CCD detector as shown in the extremely simplified view of FIG. 3. Each column of CCD pixels may represent one wavelength. There may be 5 CCD pixels (or rows) mapped to an image point (or fiber) at a particular wavelength, for example. Thus, in the case of 1024 pixels in a column, around 204-205(1024 divided by 5) image points (or linear fiber array outputs) can be accommodated. A 1D-to-2D array mapping may then organize each column of CCD back to or close to the original 2D fiber bundle arrangement so as to obtain the 2D image of the sample for the specific wavelength (also known as a 3D spectral image).

The FAST-based chemical imaging method may provide a significant speed of analysis. Using FAST, a complete chemical imaging data set can often be acquired in approximately the amount of time it takes to generate a single spectrum from a given material with a conventional non-FAST method. Fusion of FAST-generated chemical images and high-spatial resolution images generated using other modalities can provide significant insight into the morphology and chemistry of materials. Furthermore, a FAST system may provide significant instrumentation cost reduction, expanded free spectral range (UV-NIR), and optional sensitivity to polarization.

FAST enables full spectral acquisition for hundreds to thousands of spatially resolved spectra in a single image frame—dramatically increasing data acquisition rates compared to current tunable filter based technologies. Software and/or hardware may be used to extract the spatial/spectral information to reconstruct hyperspectral (Chemical Imaging) data cubes of the original object. Furthermore, FAST is a rugged technology that operates over an extensive spectral range (from UV to NIR).

In the FAST optical system embodiment of FIG. 2, a two-lens imaging configuration is shown, although the present disclosure is not limited to such a configuration, as would be obvious to those of skill in the art. The system in FIG. 2 may include a collecting lens 204, an imaging lens 203, and some optics (e.g., filters 208 and 209, described above) for laser illumination for spectroscopy, such as Raman spectroscopy. The collecting lens 204 may be a doublet for focusing the laser beam onto the sample and collecting photons from the sample, such as Raman radiations/Raman scattered photons from the sample. The collecting lens 204 may also collimate the imaging beams (e.g., the Raman photons) and project images in infinity. The imaging lens 203 may also be a doublet and may be selected in such a way that when it is used together with the collecting lens 204, images, e.g., of Raman radiations, will be formed at its final focal plane. Because the imaging beams between the collecting lens 204 and the imaging lens 203 are collimated, it may be easier to introduce one of more laser filters, such as filters 208 and/or 209, into the FAST optics as shown in FIG. 2.

Figure 9:
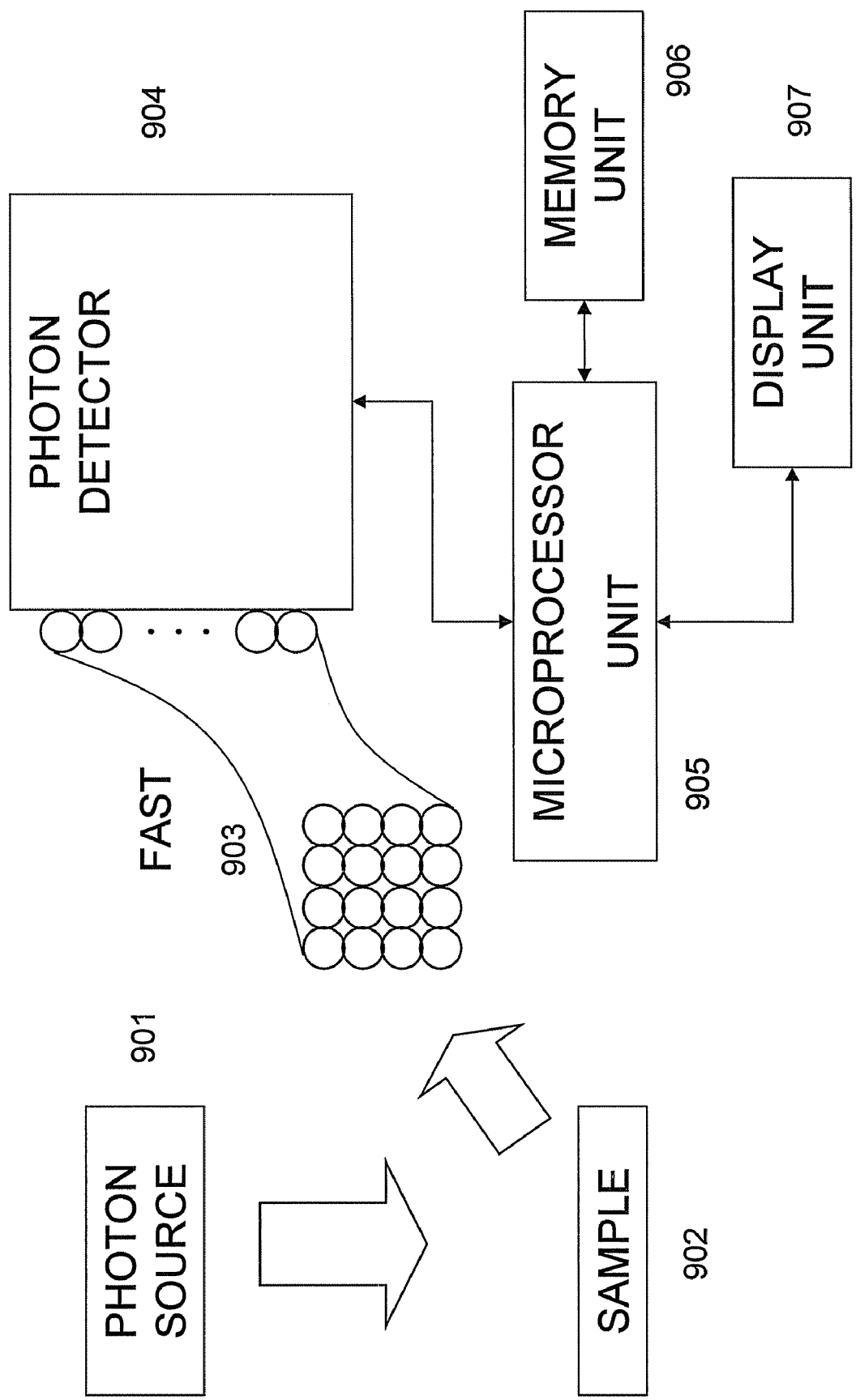
FIG. 9 is a block diagram of a system for spectral calibration according to one embodiment of the disclosure.

In one embodiment of the present disclosure, the FAST system of FIG. 1 may be used to screen or detect polymorphs present in a sample (e.g., a 96-well plate, referred to above as stage 105 in FIG. 1). The detection may be accomplished by matching spectra of the observed target sample against a set of library spectra. Thus, in case of a mixture containing polymorphs, a spectrum of a polymorph crystal may be matched against a set of library spectra of various polymorphs to identify the polymorph or polymorphs present in the mixture. In one embodiment, the library spectra of a plurality of known polymorphs of a compound may be pre-stored electronically (e.g., in a computer memory used along with the FAST system of FIG. 1, as shown in FIG. 9 discussed below). Such spectra may have been obtained in a device-independent manner (i.e., the spectra may not be taken using the FAST system selected for current polymorph screening application). In an alternative embodiment, the library spectra may be generated using the same FAST system as that being used for current polymorph screening application at hand. Hence, in such an embodiment, the library spectra may be device-dependent and, hence, may be matched more accurately with the target polymorph spectra.

In one embodiment, there may be 19 fibers in the fiber bundle. As will be obvious to those of skill in the art, the present disclosure is not limited to a 19-fiber FAST bundle and can be implemented with any number of fibers in the FAST bundle in any type of 2D orientation at the proximal, or imaging, end. The fiber bundle may be sequentially focused on each well in the 96-well plate placed on the stage 105 of FIG. 1. The stage 105 may be designed to receive samples for spectroscopic analysis. Each well may contain a plurality of polymorphs, in which case the resulting spectrum may be a combination of individual polymorph spectra. Various spectral matching techniques may be employed to identify which known polymorphs are present in the well being investigated. Also, those spectra that do not match with the library spectra may indicate presence of unknown polymorphs in the sample at hand. Such information may be useful in further analyzing the sample for detection and identification of such new polymorphs.

Figure 4:
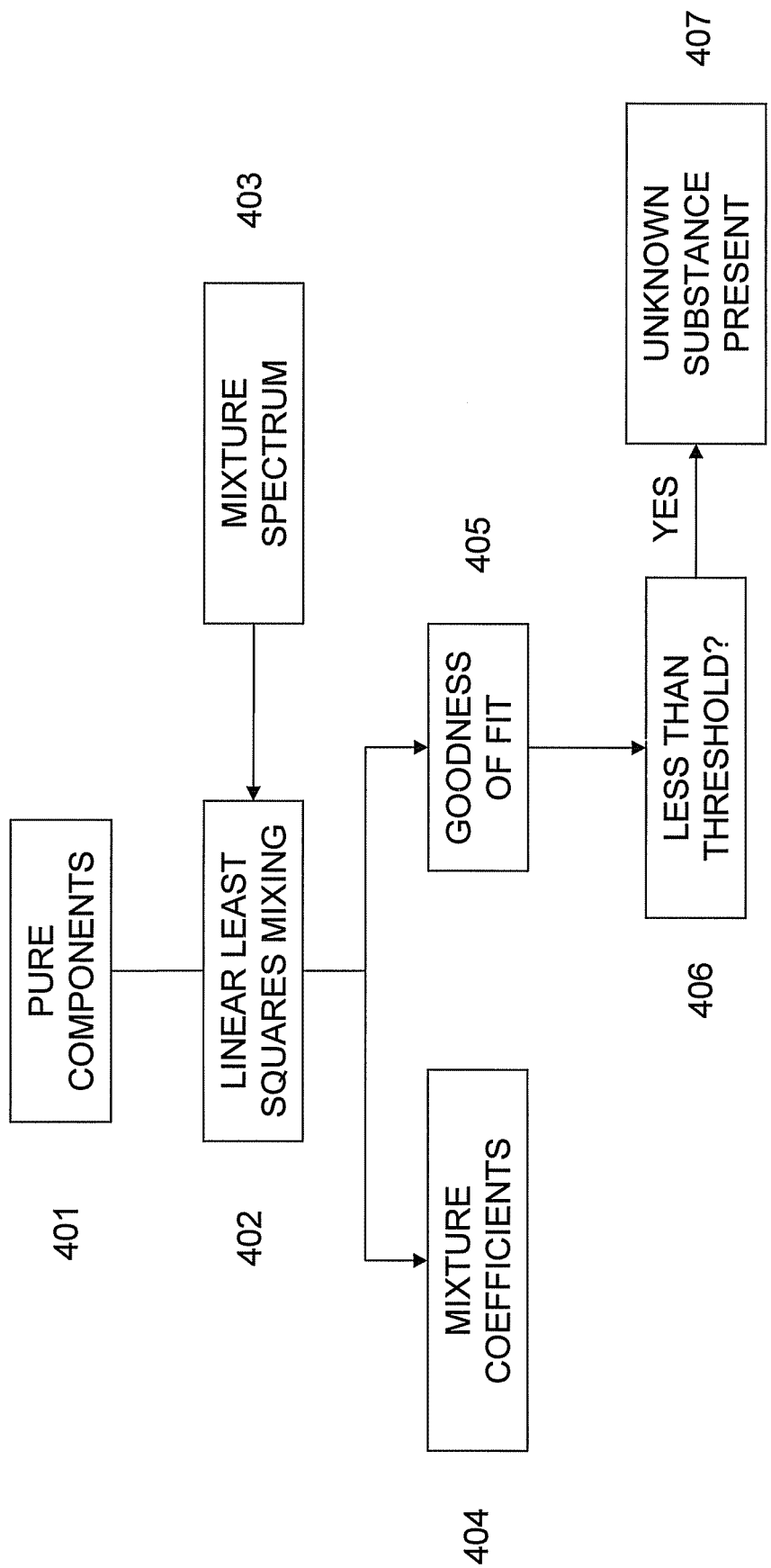
FIG. 4 is a flow chart of a method for spectral unmixing according to one embodiment of the disclosure.
Figure 5:
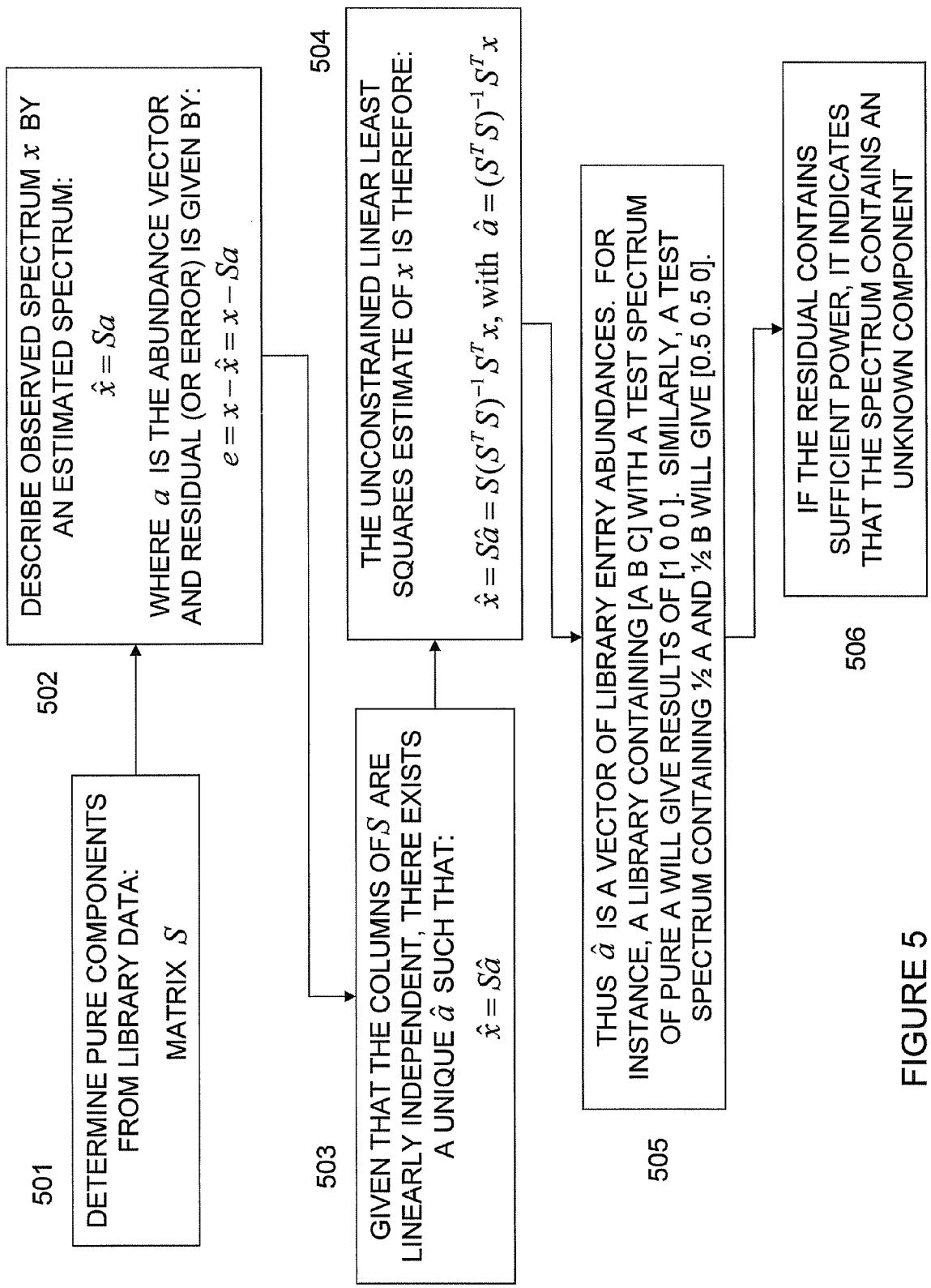
FIG. 5 is a flow chart of a method for spectral unmixing according to one embodiment of the disclosure.

In one embodiment, a linear spectral unmixing model may be used to perform spectral matching. In this model, it may be assumed that each of the 19 fiber spectra, for example, is a linear combination of the library spectra in varying proportions. FIG. 4 illustrates a block diagram broadly depicting the linear unmixing methodology according to one embodiment of the present disclosure. In block 401 pure component spectra are provided, such as from a library of spectra electronically stored in a memory device. In block 402, a linear least squares mixing algorithm is run using a mixture spectrum 403 obtained with a FAST spectroscopy system as described herein. The least squares unmixing algorithm may be an unconstrained linear least squares algorithm, a nonnegative constrained linear least squares algorithm, or other suitable unmixing algorithm as is known in the art. FIG. 5 describes an exemplary linear unmixing approach in more detail. Additional information on a linear mixing model may be found in Manolakis et al., *Hyperspectral Subpixel Target Detection Using the Linear Mixing Model*, IEEE Transaction on Geoscience and Remote Sensing, Vol. 39, No. 7, July 2001, pp. 1392-1409, the disclosure of which is incorporated herein by reference in its entirety. The output of the linear least squares mixing algorithm in block 402 may result in the obtaining of mixture coefficients 404, i.e., a relative or absolute amount of one or more of the pure component spectra 401 that make up the mixture spectrum 403. The output of the linear least squares mixing algorithm 402 may also be used for a "goodness of fit" determination in block 405. This goodness of fit determination may be an algorithm run in software and/or hardware and is used to determine how "close" the estimate of mixture coefficients is to the actual mixture of the pure components in the mixture under analysis, as will be described in more detail below. If the goodness of fit analysis is less than a predetermined threshold in block 406, then, in block 407, this may indicate that there is an unknown substance in the mixture, such as another pure component or, perhaps, that the determined mixture coefficients are inaccurate.

With attention now directed toward FIG. 5, a linear mixing model is described. In this embodiment, each of the 19 fiber spectra may be a linear combination of the library spectra. Linear spectral unmixing may be used to estimate the proportions of each library entry comprising each pixel. The residual can be analyzed for remaining peaks to identify the presence of an unknown. The steps that may be used in this analysis may be as follows: In Block 501, determine pure components from library data: matrix S. In block 502, where the goal is to describe the observed spectrum x by an estimated spectrum:

$$\hat{x} = Sa$$

where a is the abundance vector, and residual (or error) is given by:

$$e = x - \hat{x} = x - Sa$$

In block 503, given that the columns of S are linearly independent, there exists a unique $\hat{a}$ such that:

$$\hat{x} = S\hat{a}$$

In block 504, the unconstrained linear least squares estimate of x is thus:

$$\hat{x} = S\hat{a} = S(S^T S)^{-1} S^T x, \text{ with } \hat{a} = (S^T S)^{-1} S^T x$$

In block 505, thus $\hat{a}$ is a vector of library entry abundances. For instance, a library containing [A B C] with a test spectrum of pure A will give results of [1 0 0]. Similarly, a spectrum containing ½ A and ½ B will give [0.5 0.5 0]. In block 506, if the residual contains sufficient power, it indicates that the spectrum contains an unknown component.

Figure 6:
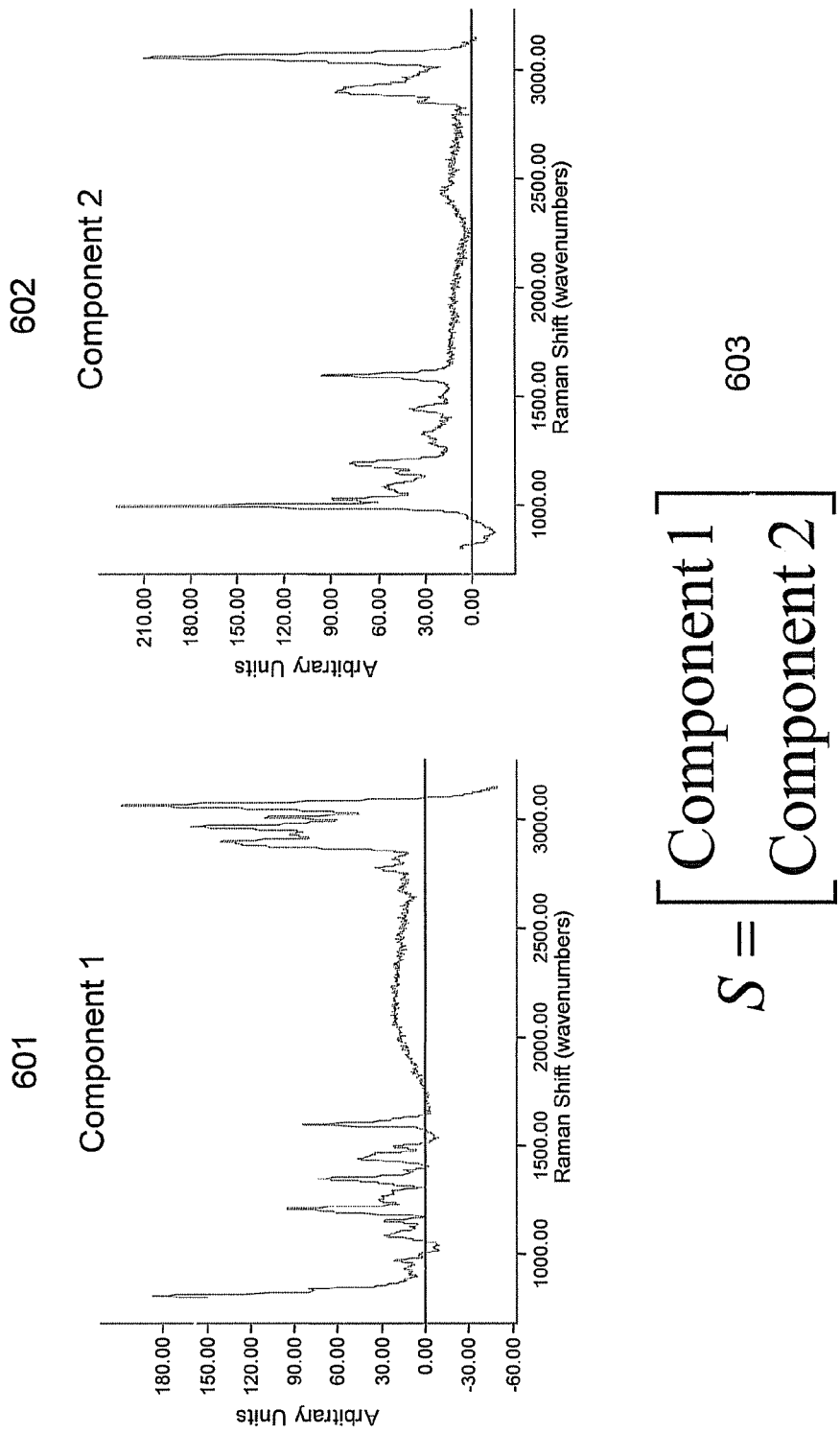
FIG. 6 illustrates an exemplary spectrum of each of two pure components.
Figure 7:
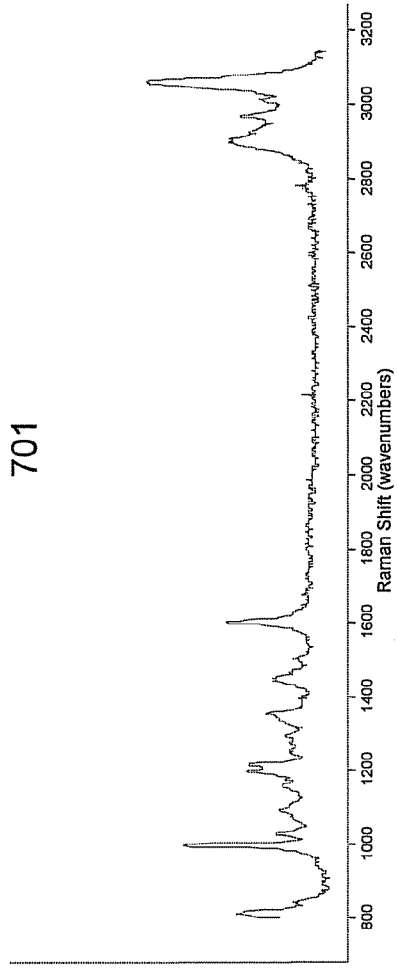
FIG. 7 illustrates an exemplary spectrum of each a mixture of the two pure components in FIG. 6.

The linear unmixing application may generate a set of mixture coefficients—represented by the abundance vector—that may indicate the proportional presence of various library spectra in the observed target spectrum. For example, in the case of the embodiment of FIG. 6, two library spectra are shown—one for each of the two library components, Component 1 (601) and Component 2 (602). The pure component matrix "S" (603) would include these component spectra as shown in FIG. 6. However, FIG. 7 shows a mixture spectrum "x" (701) that is observed from a sample using a FAST system as described herein. As discussed above with respect to FIG. 5, this mixture spectrum may be a linear combination of two or more library spectra. In the embodiment of FIGS. 6 and 7, the mixture spectrum 701 in FIG. 7 may be analyzed using a linear spectral unmixing approach, such as the one described above in reference to FIG. 5, to conclude that the mixture spectrum 701 in FIG. 7 relates to a component mixture that comprises approximately 50% of Component 1 (601 in FIG. 6) (corresponding to the mixture coefficient value of 0.4745 in the abundance vector) and approximately 50% of Component 2 (602 in FIG. 6) (corresponding to the mixture coefficient value of 0.5253 in the abundance vector). The mixture coefficient equation and values for this example are shown in FIG. 7 at 702. Thus, the mixture coefficients provide proportional presence of pure component spectra in the observed mixture spectrum.

The goodness-of-fit determination referred to above with respect to block 405 in FIG. 4 (for a target spectrum with reference to the library spectra) may also be made by calculating the $R^2$ factor as:

$$R^2 = \frac{\hat{x}^T \hat{x} - e^T e}{\hat{x}^T \hat{x}}.$$

This factor measures the goodness-of-fit for the regression. In one embodiment, any $R^2$ value that is less than a threshold of 0.9 will be marked as containing an unknown spectrum (and, hence, an unknown polymorph in the mixture under observation and analysis) as illustrated at block 407 in FIG. 4. The 0.9 threshold is chosen as an example and shall not be seen as limiting the current disclosure in any way. z The linear spectral unmixing approach according to one embodiment of the present disclosure may be desirable in a FAST-based polymorph screening application. Polymorphs typically exhibit Raman shifts in one or more peaks. Thus two distinct polymorphs may share some peaks and have some unique peaks. This uniqueness, regardless of signal origin, permits the linear independence assumptions in the linear unmixing approach discussed herein. The known least-squares optimal solution is simple to implement and, hence, can be adapted to a FAST-based polymorph screening application as discussed herein. Further, mixtures containing polymorphs can be identified more readily than through "manual" subtraction and spectral peak matching.

In another embodiment, the present disclosure contemplates using the target factor based spectral unmixing in a FAST based polymorph screening application. The target factor based spectral unmixing is described in the pending U.S. patent application (Ser. No. 10/812,233; Filing Date: Mar. 29, 2004) titled "Method for Identifying Components of a Mixture via Spectral Analysis", the disclosure of this patent application is hereby incorporated by reference in its entirety. Thus, in place of the linear spectral unmixing discussed above, the target factor based spectral analysis methodology may be used to detect/identify any known or unknown polymorphs present in a component mixture containing polymorphs.

Figure 8:
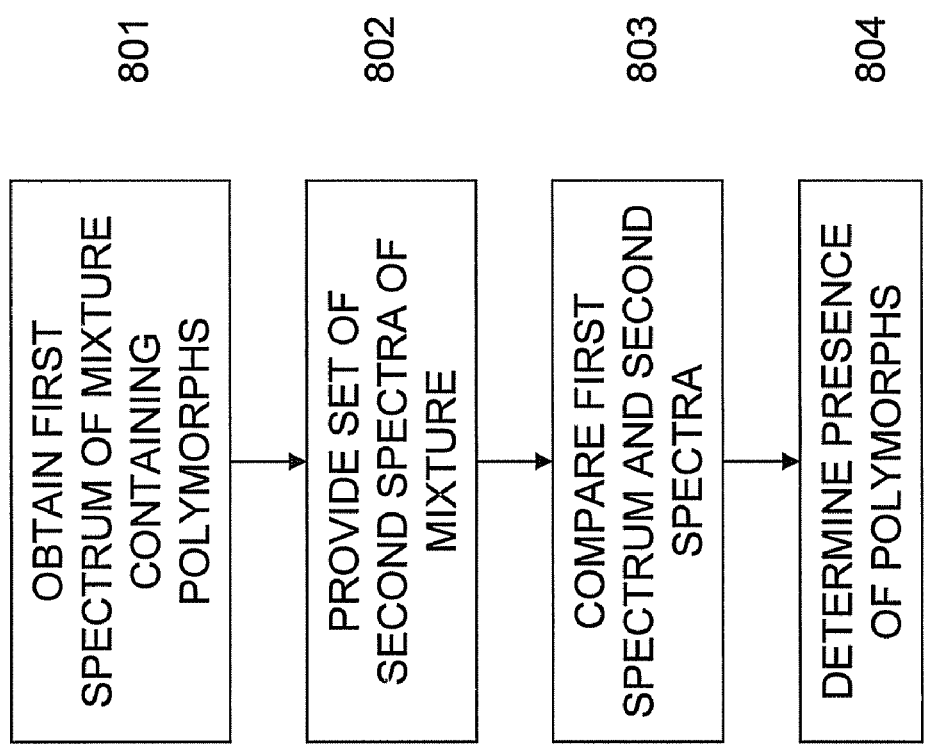
FIG. 8 is a flow chart of a method for spectral unmixing according to one embodiment of the disclosure.

FIG. 8 is a flow diagram of a methodology according to an embodiment of the present disclosure. At block 801 a first spectrum of a mixture containing polymorphs is obtained. At block 802, a set of second spectra, such as library reference spectra, of the mixture are provided. At block 803, a comparison is made between the first spectrum and the second spectra. At block 804, a determination is made of the presence of one or more polymorphs in the mixture, based on the comparison in block 803.

FIG. 9 illustrates, in block diagram form, an exemplary system according to an embodiment of the present disclosure. A photon source 901 may illuminate with first photons a mixture, sample 902, which may contain polymorphs of a compound, to thereby produce second photons. A fiber array spectral translator 903, having plural fibers receives the second photons and directs them to a photon detector 904 which is operatively connected to the fiber array spectral translator. The photon detector 904 detects the second photons to thereby obtain a first spectrum. A microprocessor unit 905 is operatively connected to the photon detector 904 and to a memory unit 906. The memory unit 906 may store a set of second spectra where each spectrum of the set of second spectra may be representative of a different polymorph of the compound (sample 902). The microprocessor unit 905 may compare the first spectrum with the set of second spectra to thereby determine the presence of one or more polymorphs in the mixture based on said comparison.

Figure 10:
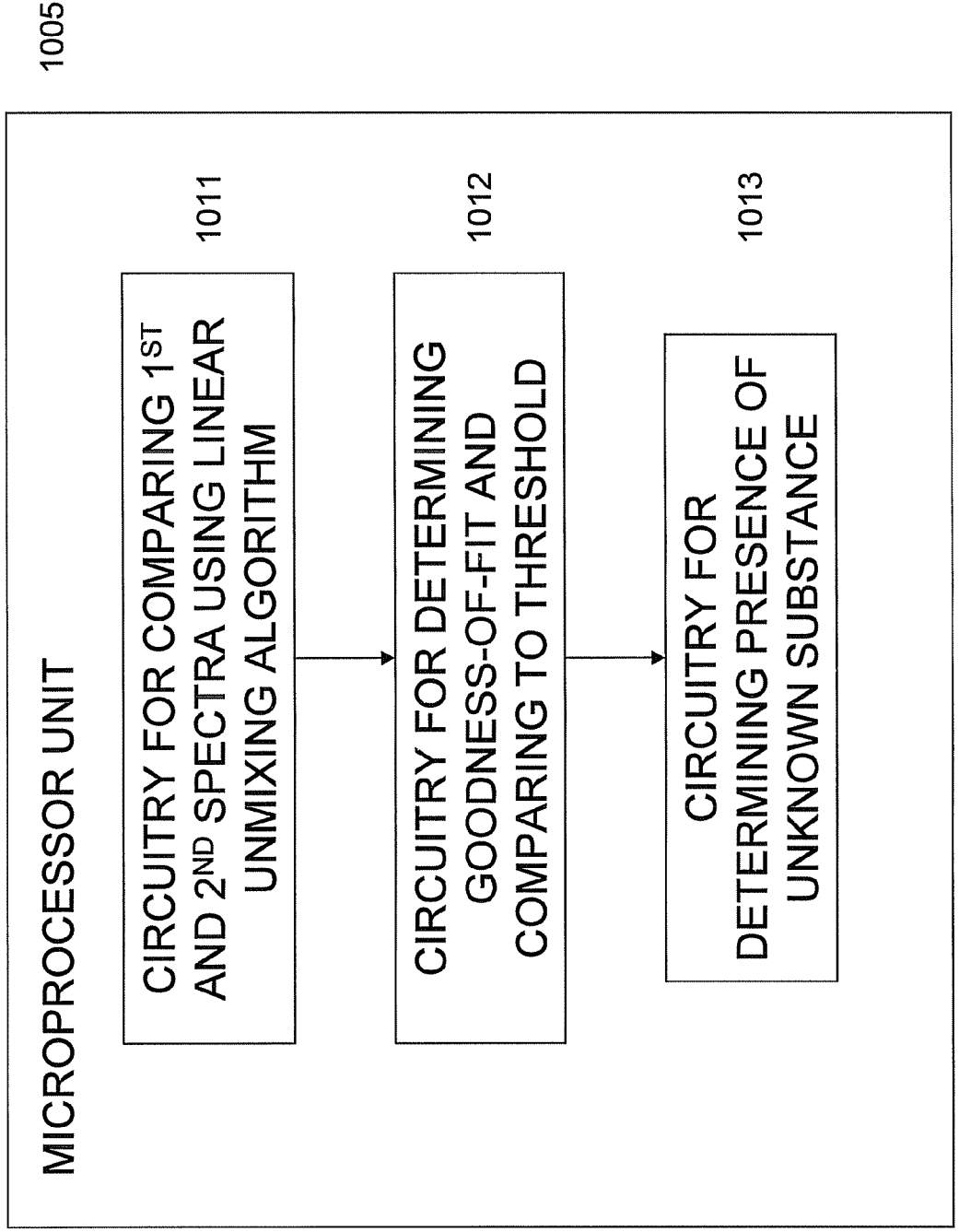
FIG. 10 is a block diagram of a microprocessor in the system of FIG. 9 according to one embodiment of the disclosure.

FIG. 10 is a block diagram of an embodiment of the disclosure showing circuitry in the microprocessor unit for performing certain functions. It will be understood by those of skill in the art that the functions may be performed in hardware (e.g., circuitry), software, or some combination of the two. It will be further understood that the circuitry and/or software need not be in separate discrete units as shown in FIG. 10. The microprocessor unit 1005 is the same as the microprocessor unit 905 in FIG. 9. In the embodiment shown in FIG. 10, microprocessor unit 1005 contains circuitry 1011 for comparing a first spectrum with a set of second spectra using a linear spectral unmixing algorithm to thereby determine a set of mixture coefficients so as to determine the presence of one or more polymorphs in said mixture based on said comparison; circuitry 1012 for determining a goodness-of-fit factor and comparing the goodness-of-fit factor to a predetermined threshold; and circuitry 1013 for determining the presence of an unknown substance in a mixture if the goodness-of-fit factor is less than the predetermined threshold.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

We claim:

1. A method for spectral unmixing, comprising:
   obtaining a first spectrum of a mixture containing polymorphs of a compound using a photon detector and a fiber array spectral translator having plural fibers;
   providing a set of second spectra wherein each spectrum of said set of second spectra is representative of a different polymorph of said compound;
   comparing said first spectrum with said set of second spectra; and
   determining the presence of one or more polymorphs in said mixture based on said comparison.

2. The method of claim 1 wherein said photon detector is selected from the group consisting of: charge-coupled device ("CCD"), complementary metal oxide semiconductor ("CMOS") detector, and focal plane array sensor.

3. The method of claim 1 wherein one of said spectrum of said set of second spectra is a predefined library spectrum.

4. The method of claim 3 wherein said predefined library spectrum is obtained by using said photon detector and said fiber array spectral translator.

5. The method of claim 1 wherein said first spectrum is obtained from one of said plural fibers in said fiber array spectral translator.

6. The method of claim 1 wherein the comparing comprises using a linear spectral unmixing algorithm.

7. The method of claim 6 wherein said linear spectral unmixing algorithm is a linear least squares unmixing algorithm.

8. The method of claims 7 wherein said linear least squares unmixing algorithm is one of an unconstrained linear least squares algorithm or a non-negative constrained linear least squares algorithm.

9. The method of claim 6 wherein the determining results in a set of mixture coefficients.

10. The method of claim 1 further comprising determining a goodness-of-fit factor.

11. The method of claim 10 further comprising comparing said goodness-of-fit factor to a predetermined threshold.

12. The method of claim 11 further comprising determining the presence of an unknown substance in said mixture if said goodness-of-fit factor is less than said predetermined threshold.

13. A system for spectral unmixing, comprising:
    a photon source for illuminating with first photons a mixture containing polymorphs of a compound to thereby produce second photons;
    a fiber array spectral translator having plural fibers, wherein said fiber array spectral translator receives said second photons;
    a photon detector operatively connected to said fiber array spectral translator, wherein said photon detector detects said second photons to thereby obtain a first spectrum; and
    a microprocessor unit operatively connected to said photon detector and to a memory unit, wherein said memory unit stores a set of second spectra wherein each spectrum of said set of second spectra is representative of a different polymorph of said compound, and wherein said microprocessor compares said first spectrum with said set of second spectra to thereby determine the presence of one or more polymorphs in said mixture based on said comparison.

14. The system of claim 13 wherein said photon detector is selected from the group consisting of: charge-coupled device ("CCD"), complementary metal oxide semiconductor ("CMOS") detector, and focal plane array sensor.

15. The system of claim 13 wherein one of said spectrum of said set of second spectra is a predefined library spectrum.

16. The system of claim 15 wherein said predefined library spectrum is obtained by using said photon detector and said fiber array spectral translator.

17. The system of claim 13 wherein said first spectrum is obtained from one of said plural fibers in said fiber array spectral translator.

18. The system of claim 13 wherein said microprocessor compares said first spectrum with said set of second spectra using a linear spectral unmixing algorithm.

19. The system of claim 18 wherein said linear spectral unmixing algorithm is a linear least squares unmixing algorithm.

20. The system of claims 19 wherein said linear least squares unmixing algorithm is one of an unconstrained linear least squares algorithm or a non-negative constrained linear least squares algorithm.

21. The system of claim 18 wherein said microprocessor determines said presence of one or more polymorphs by determining a set of mixture coefficients.

22. The system of claim 13 wherein said microprocessor further determines a goodness-of-fit factor.

23. The system of claim 22 wherein said microprocessor further compares said goodness-of-fit factor to a predetermined threshold.

24. The system of claim 23 wherein said microprocessor further determines the presence of an unknown substance in said mixture if said goodness-of-fit factor is less than said predetermined threshold.

25. The system of claim 24 wherein said microprocessor runs a software program for comparing said first spectrum with said set of second spectra, determining said goodness-of-fit factor, comparing said goodness-of-fit factor to said predetermined threshold, and determining the presence of an unknown substance in said mixture if said goodness-of-fit factor is less than said predetermined threshold.

26. The system of claim 13 wherein said microprocessor runs a software program for comparing said first spectrum with said set of second spectra.

27. A method for spectral unmixing, comprising:
    obtaining a first spectrum of a mixture containing polymorphs of a compound using a photon detector and a fiber array spectral translator having plural fibers, wherein said first spectrum is obtained from one of said plural fibers;
    providing a set of second spectra wherein each spectrum of said set of second spectra is representative of a different polymorph of said compound;

comparing said first spectrum with said set of second spectra using a linear spectral unmixing algorithm;

determining a set of mixture coefficients to thereby determine the presence of one or more polymorphs in said mixture;

determining a goodness-of-fit factor and comparing said goodness-of-fit factor to a predetermined threshold; and determining the presence of an unknown substance in said mixture if said goodness-of-fit factor is less than said predetermined threshold.

28. The method of claim 27 wherein said photon detector is selected from the group consisting of: charge-coupled device ("CCD"), complementary metal oxide semiconductor ("CMOS") detector, and focal plane array sensor.

29. The method of claim 27 wherein one of said spectrum of said set of second spectra is a predefined library spectrum.

30. The method of claim 29 wherein said predefined library spectrum is obtained by using said photon detector and said fiber array spectral translator.

31. The method of claim 27 wherein said linear spectral unmixing algorithm is a linear least squares unmixing algorithm.

32. The method of claims 31 wherein said linear least squares unmixing algorithm is one of an unconstrained linear least squares algorithm or a non-negative constrained linear least squares algorithm.

33. A system for spectral unmixing, comprising:

a photon source for illuminating with first photons a mixture containing polymorphs of a compound to thereby produce second photons;

a fiber array spectral translator having plural fibers, wherein one fiber of said fiber array spectral translator receives said second photons;

a photon detector operatively connected to said one fiber of said fiber array spectral translator, wherein said photon detector detects said second photons to thereby obtain a first spectrum; and a microprocessor unit operatively connected to said photon detector and to a memory unit, wherein said memory unit stores a set of second spectra wherein each spectrum of said set of second spectra is representative of a different polymorph of said compound, and wherein said microprocessor includes:

circuitry for comparing said first spectrum with said set of second spectra using a linear spectral unmixing algorithm to thereby determine a set of mixture coefficients so as to determine the presence of one or more polymorphs in said mixture based on said comparison;

circuitry for determining a goodness-of-fit factor and comparing said goodness-of-fit factor to a predetermined threshold; and circuitry for determining the presence of an unknown substance in said mixture if said goodness-of-fit factor is less than said predetermined threshold.

34. The system of claim 33 wherein said photon detector is selected from the group consisting of: charge-coupled device ("CCD"), complementary metal oxide semiconductor ("CMOS") detector, and focal plane array sensor.

35. The system of claim 33 wherein one of said spectrum of said set of second spectra is a predefined library spectrum.

36. The system of claim 35 wherein said predefined library spectrum is obtained by using said photon detector and said fiber array spectral translator.

37. The system of claim 33 wherein said linear spectral unmixing algorithm is a linear least squares unmixing algorithm.

38. The system of claims 37 wherein said linear least squares unmixing algorithm is one of an unconstrained linear least squares algorithm or a non-negative constrained linear least squares algorithm.

39. A system for spectral unmixing, comprising:

a photon source for illuminating with first photons a mixture containing polymorphs of a compound to thereby produce second photons;

a fiber array spectral translator having plural fibers, wherein one fiber of said fiber array spectral translator receives said second photons;

a photon detector operatively connected to said one fiber of said fiber array spectral translator, wherein said photon detector detects said second photons to thereby obtain a first spectrum; and a microprocessor unit operatively connected to said photon detector and to a memory unit, wherein said memory unit stores a set of second spectra wherein each spectrum of said set of second spectra is representative of a different polymorph of said compound, and wherein said microprocessor runs a software program for:

comparing said first spectrum with said set of second spectra using a linear spectral unmixing algorithm to thereby determine a set of mixture coefficients so as to determine the presence of one or more polymorphs in said mixture based on said comparison;

determining a goodness-of-fit factor and comparing said goodness-of-fit factor to a predetermined threshold; and determining the presence of an unknown substance in said mixture if said goodness-of-fit factor is less than said predetermined threshold.

40. The system of claim 39 wherein said photon detector is selected from the group consisting of: charge-coupled device ("CCD"), complementary metal oxide semiconductor ("CMOS") detector, and focal plane array sensor.

41. The system of claim 39 wherein one of said spectrum of said set of second spectra is a predefined library spectrum.

42. The system of claim 41 wherein said predefined library spectrum is obtained by using said photon detector and said fiber array spectral translator.

43. The system of claim 39 wherein said linear spectral unmixing algorithm is a linear least squares unmixing algorithm.

44. The system of claims 43 wherein said linear least squares unmixing algorithm is one of an unconstrained linear least squares algorithm or a non-negative constrained linear least squares algorithm.

* * * * *